(12) United States Patent
Sakanyan et al.

(10) Patent No.: US 6,897,048 B2
(45) Date of Patent: May 24, 2005

(54) MICROORGANISMS AND METHOD FOR L-ARGININE PRODUCTION BY FERMENTATION

(75) Inventors: Vehary Sakanyan, Orvault (FR); Frédéric Marc, Saint-Nazaire (FR); Anitchka Hovsepyan, Yerevan (AM); Michèle Lecocq, Nantes (FR)

(73) Assignee: Ajinomoto Co. Inc, Tokyo (JP)

( * ) Notice: Subject to any disclaimer, the term of this patent is extended or adjusted under 35 U.S.C. 154(b) by 0 days.

(21) Appl. No.: 09/983,931

(22) Filed: Oct. 26, 2001

(65) Prior Publication Data

US 2002/0098555 A1 Jul. 25, 2002

(30) Foreign Application Priority Data

Oct. 27, 2000 (EP) ............................................. 00403003

(51) Int. Cl.⁷ ............................ C12P 13/10; C12N 9/12; C12N 1/20; C12N 15/00; C07H 21/04

(52) U.S. Cl. .................... 435/114; 435/193; 435/252.3; 435/320.1; 435/832; 435/942; 536/23.2

(58) Field of Search ................................. 435/114, 193, 435/252.3, 320.1, 822, 832, 942; 536/23.2

(56) References Cited

PUBLICATIONS

Sakanyan et al. [J. Gen Microbiol. (1993) 139, 392–402].*

* cited by examiner

*Primary Examiner*—Tekchand Saidha
(74) *Attorney, Agent, or Firm*—Oblon, Spivak, McClelland, Maier & Neustadt, P.C.

(57) ABSTRACT

The present invention relates to a microorganism having an L-arginine producing ability where the microorganism synthesizes L-arginine through the biosynthetic linear or cyclic pathway and contains a recombinant DNA containing the argJ gene encoding an enzyme having ornithine acetyltransferase activity.

18 Claims, 1 Drawing Sheet

SEQUENCE LISTING

<160> NUMBER OF SEQ ID NOS: 12

<210> SEQ ID NO 1
<211> LENGTH: 1233
<212> TYPE: DNA
<213> ORGANISM: Bacillus stearothermophilus
<220> FEATURE:
<221> NAME/KEY: CDS
<222> LOCATION: (1)..(1233)
<223> OTHER INFORMATION:

<400> SEQUENCE: 1

```
atg acg atc aca aaa caa acg ggg caa gtg acg gcg gtc gcc gat gga      48
Met Thr Ile Thr Lys Gln Thr Gly Gln Val Thr Ala Val Ala Asp Gly
 1               5                  10                  15 aca gtg gtt acg ccg gaa gga ttt caa gcg gcc ggg gtg aat gcc ggg      96
Thr Val Val Thr Pro Glu Gly Phe Gln Ala Ala Gly Val Asn Ala Gly
                 20                  25                  30 ctg cgc tat tcg aaa aac gat tta ggg gtt att cta tgc gac gtg ccc     144
Leu Arg Tyr Ser Lys Asn Asp Leu Gly Val Ile Leu Cys Asp Val Pro
             35                  40                  45 gct tcg gcg gcg gcg gtg tat acg caa agc cat ttt cag gcg gcg ccg     192
Ala Ser Ala Ala Ala Val Tyr Thr Gln Ser His Phe Gln Ala Ala Pro
         50                  55                  60 ctc aaa gtg acg cag gcg agc ctc gct gta gaa caa aaa ttg cag gcg     240
Leu Lys Val Thr Gln Ala Ser Leu Ala Val Glu Gln Lys Leu Gln Ala
 65                  70                  75                  80 gtc atc gtc aac agg ccg tgc gcg aac gcc tgc acc ggt gcg caa ggg     288
Val Ile Val Asn Arg Pro Cys Ala Asn Ala Cys Thr Gly Ala Gln Gly
                 85                  90                  95 ctc aag gac gct tat gaa atg cgt gag ttg tgc gcg aaa cag ttt ggc     336
Leu Lys Asp Ala Tyr Glu Met Arg Glu Leu Cys Ala Lys Gln Phe Gly
            100                 105                 110 ctg gcg ctg cac cat gtg gcc gtc gct tca acg ggc gta atc ggg gaa     384
Leu Ala Leu His His Val Ala Val Ala Ser Thr Gly Val Ile Gly Glu
        115                 120                 125 tat ttg ccg atg gaa aaa att cgc gcc ggc atc aaa cag ctt gtt cca     432
Tyr Leu Pro Met Glu Lys Ile Arg Ala Gly Ile Lys Gln Leu Val Pro
    130                 135                 140 ggg gtg acg atg gcg gat gcg gag gcg ttt caa acg gcg att tta acg     480
Gly Val Thr Met Ala Asp Ala Glu Ala Phe Gln Thr Ala Ile Leu Thr
145                 150                 155                 160 acc gat acg gtg atg aag cgc gct tgt tac caa aca acg atc gac ggg     528
Thr Asp Thr Val Met Lys Arg Ala Cys Tyr Gln Thr Thr Ile Asp Gly
                165                 170                 175 aaa acg gtc acc gtc ggc gga gcg gcg aaa ggg tcg ggg atg atc cat     576
Lys Thr Val Thr Val Gly Gly Ala Ala Lys Gly Ser Gly Met Ile His
            180                 185                 190 ccg aac atg gcg acg atg ctc gca ttc atc acg acg gat gcc aat gtt     624
Pro Asn Met Ala Thr Met Leu Ala Phe Ile Thr Thr Asp Ala Asn Val
        195                 200                 205 tcg tcg ccg gtg ctg cac gcg gcg ctg cgg tcg att acg gac gtt tcg     672
Ser Ser Pro Val Leu His Ala Ala Leu Arg Ser Ile Thr Asp Val Ser
    210                 215                 220 ttt aac caa att acg gtc gac ggc gat acg tcg aca aat gat atg gtc     720
Phe Asn Gln Ile Thr Val Asp Gly Asp Thr Ser Thr Asn Asp Met Val
225                 230                 235                 240 gtc gtg atg gca agc ggt ctt gct gga aat gat gag ttg acg ccg gat     768
Val Val Met Ala Ser Gly Leu Ala Gly Asn Asp Glu Leu Thr Pro Asp
                245                 250                 255
```

```
cat ccg gac tgg gaa aac ttt tat gag gcg ctg cgg aaa acg tgc gaa      816
His Pro Asp Trp Glu Asn Phe Tyr Glu Ala Leu Arg Lys Thr Cys Glu
        260                 265                 270 gat ttg gcg aag caa atc gcc aaa gac ggc gag ggg gcg acg aag ctc      864
Asp Leu Ala Lys Gln Ile Ala Lys Asp Gly Glu Gly Ala Thr Lys Leu
        275                 280                 285 att gaa gtg cgc gtg cgc ggc gcg aaa acg gat gag gaa gcg aaa aaa      912
Ile Glu Val Arg Val Arg Gly Ala Lys Thr Asp Glu Glu Ala Lys Lys
    290                 295                 300 atc gcc aag caa atc gtc ggc tct aac tta gtg aaa acg gcc gtt tac      960
Ile Ala Lys Gln Ile Val Gly Ser Asn Leu Val Lys Thr Ala Val Tyr
305                 310                 315                 320 ggc gcg gac gcc aac tgg ggg cgg atc atc ggc gcg atc ggt tat tcg     1008
Gly Ala Asp Ala Asn Trp Gly Arg Ile Ile Gly Ala Ile Gly Tyr Ser
                325                 330                 335 gat gcc gaa gtg aac ccg gac aac gtc gat gtc gcc atc ggg ccg atg     1056
Asp Ala Glu Val Asn Pro Asp Asn Val Asp Val Ala Ile Gly Pro Met
            340                 345                 350 gtg atg ctg aaa gga agc gag ccg cag ccg ttc tcg gaa gaa gaa gcg     1104
Val Met Leu Lys Gly Ser Glu Pro Gln Pro Phe Ser Glu Glu Glu Ala
        355                 360                 365 gcg gcg tat ttg caa caa gag acg gtc gtc att gag gtc gat ttg cat     1152
Ala Ala Tyr Leu Gln Gln Glu Thr Val Val Ile Glu Val Asp Leu His
        370                 375                 380 ata ggc gat ggt gtc ggc gtt gcg tgg ggc tgc gat ttg aca tac gat     1200
Ile Gly Asp Gly Val Gly Val Ala Trp Gly Cys Asp Leu Thr Tyr Asp
385                 390                 395                 400 tat gtg aaa att aac gcc agc tat cgg acg taa                          1233
Tyr Val Lys Ile Asn Ala Ser Tyr Arg Thr
                405                 410

<210> SEQ ID NO 2
<211> LENGTH: 410
<212> TYPE: PRT
<213> ORGANISM: Bacillus stearothermophilus

<400> SEQUENCE: 2

Met Thr Ile Thr Lys Gln Thr Gly Gln Val Thr Ala Val Ala Asp Gly
1               5                   10                  15

Thr Val Val Thr Pro Glu Gly Phe Gln Ala Ala Gly Val Asn Ala Gly
                20                  25                  30

Leu Arg Tyr Ser Lys Asn Asp Leu Gly Val Ile Leu Cys Asp Val Pro
            35                  40                  45

Ala Ser Ala Ala Ala Val Tyr Thr Gln Ser His Phe Gln Ala Ala Pro
        50                  55                  60

Leu Lys Val Thr Gln Ala Ser Leu Ala Val Glu Gln Lys Leu Gln Ala
65                  70                  75                  80

Val Ile Val Asn Arg Pro Cys Ala Asn Ala Cys Thr Gly Ala Gln Gly
                85                  90                  95

Leu Lys Asp Ala Tyr Glu Met Arg Glu Leu Cys Ala Lys Gln Phe Gly
            100                 105                 110

Leu Ala Leu His His Val Ala Val Ala Ser Thr Gly Val Ile Gly Glu
        115                 120                 125

Tyr Leu Pro Met Glu Lys Ile Arg Ala Gly Ile Lys Gln Leu Val Pro
    130                 135                 140

Gly Val Thr Met Ala Asp Ala Glu Ala Phe Gln Thr Ala Ile Leu Thr
145                 150                 155                 160
```

```
Thr Asp Thr Val Met Lys Arg Ala Cys Tyr Gln Thr Thr Ile Asp Gly
            165                 170                 175

Lys Thr Val Thr Val Gly Gly Ala Ala Lys Gly Ser Gly Met Ile His
        180                 185                 190

Pro Asn Met Ala Thr Met Leu Ala Phe Ile Thr Thr Asp Ala Asn Val
            195                 200                 205

Ser Ser Pro Val Leu His Ala Ala Leu Arg Ser Ile Thr Asp Val Ser
        210                 215                 220

Phe Asn Gln Ile Thr Val Asp Gly Asp Thr Ser Thr Asn Asp Met Val
225                 230                 235                 240

Val Val Met Ala Ser Gly Leu Ala Gly Asn Asp Glu Leu Thr Pro Asp
            245                 250                 255

His Pro Asp Trp Glu Asn Phe Tyr Glu Ala Leu Arg Lys Thr Cys Glu
            260                 265                 270

Asp Leu Ala Lys Gln Ile Ala Lys Asp Gly Glu Gly Ala Thr Lys Leu
        275                 280                 285

Ile Glu Val Arg Val Arg Gly Ala Lys Thr Asp Glu Glu Ala Lys Lys
    290                 295                 300

Ile Ala Lys Gln Ile Val Gly Ser Asn Leu Val Lys Thr Ala Val Tyr
305                 310                 315                 320

Gly Ala Asp Ala Asn Trp Gly Arg Ile Ile Gly Ala Ile Gly Tyr Ser
            325                 330                 335

Asp Ala Glu Val Asn Pro Asp Asn Val Asp Val Ala Ile Gly Pro Met
        340                 345                 350

Val Met Leu Lys Gly Ser Glu Pro Gln Pro Phe Ser Glu Glu Glu Ala
            355                 360                 365

Ala Ala Tyr Leu Gln Gln Glu Thr Val Val Ile Glu Val Asp Leu His
        370                 375                 380

Ile Gly Asp Gly Val Gly Val Ala Trp Gly Cys Asp Leu Thr Tyr Asp
385                 390                 395                 400

Tyr Val Lys Ile Asn Ala Ser Tyr Arg Thr
            405                 410

<210> SEQ ID NO 3
<211> LENGTH: 1194
<212> TYPE: DNA
<213> ORGANISM: Thermotoga neapolitana
<220> FEATURE:
<221> NAME/KEY: CDS
<222> LOCATION: (1)..(1194)
<223> OTHER INFORMATION:

<400> SEQUENCE: 3 gtg ttc gtt ccg agg gga ttc agc tac gcg gga gta cac tgc aga ata      48
Val Phe Val Pro Arg Gly Phe Ser Tyr Ala Gly Val His Cys Arg Ile
1               5                   10                  15 aag aga aaa agg aaa gac ctc ggt atc atc ttc tct gaa gtg ccc tgc      96
Lys Arg Lys Arg Lys Asp Leu Gly Ile Ile Phe Ser Glu Val Pro Cys
            20                  25                  30 acc gcc gcc ggg gtt ttc acc acg aac gtt gtg aag gct gca ccc gtg    144
Thr Ala Ala Gly Val Phe Thr Thr Asn Val Val Lys Ala Ala Pro Val
        35                  40                  45 atc tac gac atg gag att ctg ggg aaa aat cct tct gga atc aga gcg    192
Ile Tyr Asp Met Glu Ile Leu Gly Lys Asn Pro Ser Gly Ile Arg Ala
    50                  55                  60 att acc gtg aac agc ggt gta gcg aac gcc tgc acg gga gaa cag gga    240
Ile Thr Val Asn Ser Gly Val Ala Asn Ala Cys Thr Gly Glu Gln Gly
```

-continued

| | | | | | | | | | | | | |
|---|---|---|---|---|---|---|---|---|---|---|---|---|
| 65 | | | | 70 | | | | 75 | | | | 80 |
| atg | atc | aac | gca | aga | agg | atg | gcg | gag | aaa | acg | gca | aaa | gaa | ctg | aac | 288 |
| Met | Ile | Asn | Ala | Arg | Arg | Met | Ala | Glu | Lys | Thr | Ala | Lys | Glu | Leu | Asn |
| | | | | 85 | | | | | 90 | | | | | 95 | |

| atc | ccc | gtt | gaa | agc | gtc | ctt | gtg | ttt | tca | aca | gga | gtg | ata | ggt | gtt | 336 |
| Ile | Pro | Val | Glu | Ser | Val | Leu | Val | Phe | Ser | Thr | Gly | Val | Ile | Gly | Val |
| | | | 100 | | | | | 105 | | | | | 110 | | |

| caa | ctt | cca | atg | gaa | aaa | gtg | gag | tcg | ggg | att | gaa | gag | gcg | gtg | aag | 384 |
| Gln | Leu | Pro | Met | Glu | Lys | Val | Glu | Ser | Gly | Ile | Glu | Glu | Ala | Val | Lys |
| | | | 115 | | | | | 120 | | | | | 125 | | |

| aac | ctc | tcg | aaa | gac | cct | gtt | ccc | ttt | gca | gag | gcc | atc | atg | aca | acg | 432 |
| Asn | Leu | Ser | Lys | Asp | Pro | Val | Pro | Phe | Ala | Glu | Ala | Ile | Met | Thr | Thr |
| | 130 | | | | | 135 | | | | | 140 | | | | |

| gac | acg | aag | ata | aag | atc | cac | agc | aaa | aaa | gtg | acg | ata | gaa | ggg | aaa | 480 |
| Asp | Thr | Lys | Ile | Lys | Ile | His | Ser | Lys | Lys | Val | Thr | Ile | Glu | Gly | Lys |
| 145 | | | | | 150 | | | | | 155 | | | | | 160 |

| gag | atc | acc | gtc | ctt | gga | ata | gca | aag | ggc | tcc | ggt | atg | ata | cat | ccc | 528 |
| Glu | Ile | Thr | Val | Leu | Gly | Ile | Ala | Lys | Gly | Ser | Gly | Met | Ile | His | Pro |
| | | | | 165 | | | | | 170 | | | | | 175 | |

| aac | atg | gcg | acg | atg | ctc | tct | ttc | ata | acg | acc | gat | gcg | aat | gtt | tct | 576 |
| Asn | Met | Ala | Thr | Met | Leu | Ser | Phe | Ile | Thr | Thr | Asp | Ala | Asn | Val | Ser |
| | | | 180 | | | | | 185 | | | | | 190 | | |

| gag | gat | gct | ctg | aaa | aaa | ctt | ctg | aag | atc | tct | gtc | gac | gat | tcc | tac | 624 |
| Glu | Asp | Ala | Leu | Lys | Lys | Leu | Leu | Lys | Ile | Ser | Val | Asp | Asp | Ser | Tyr |
| | | | 195 | | | | | 200 | | | | | 205 | | |

| aac | atg | atc | gat | gtc | gac | ggt | gat | aca | agc | aca | aac | gac | atg | gtg | atc | 672 |
| Asn | Met | Ile | Asp | Val | Asp | Gly | Asp | Thr | Ser | Thr | Asn | Asp | Met | Val | Ile |
| | 210 | | | | | 215 | | | | | 220 | | | | |

| ata | ctc | gca | aat | gga | ctt | gca | gga | aac | gca | ccc | att | cag | gag | gaa | acc | 720 |
| Ile | Leu | Ala | Asn | Gly | Leu | Ala | Gly | Asn | Ala | Pro | Ile | Gln | Glu | Glu | Thr |
| 225 | | | | | 230 | | | | | 235 | | | | | 240 |

| gat | ggt | ttc | tgg | aag | ctt | tat | gag | gcc | gta | cac | gaa | gtc | aac | cag | gtc | 768 |
| Asp | Gly | Phe | Trp | Lys | Leu | Tyr | Glu | Ala | Val | His | Glu | Val | Asn | Gln | Val |
| | | | | 245 | | | | | 250 | | | | | 255 | |

| ctt | gcg | gaa | aaa | att | gtg | gag | gac | ggg | gag | ggt | gcc | aca | aag | gtg | ata | 816 |
| Leu | Ala | Glu | Lys | Ile | Val | Glu | Asp | Gly | Glu | Gly | Ala | Thr | Lys | Val | Ile |
| | | | 260 | | | | | 265 | | | | | 270 | | |

| gaa | gtg | gaa | gtg | aga | aat | gct | ccg | gac | aga | aac | tct | gct | cgt | ttg | att | 864 |
| Glu | Val | Glu | Val | Arg | Asn | Ala | Pro | Asp | Arg | Asn | Ser | Ala | Arg | Leu | Ile |
| | | | 275 | | | | | 280 | | | | | 285 | | |

| gca | cgg | gcg | atc | gtc | tct | tcg | aat | ctt | gtg | aag | cca | gcc | atc | tac | ggt | 912 |
| Ala | Arg | Ala | Ile | Val | Ser | Ser | Asn | Leu | Val | Lys | Pro | Ala | Ile | Tyr | Gly |
| | | 290 | | | | | 295 | | | | | 300 | | | |

| gaa | gat | gca | aac | tgg | gga | agg | gtg | ata | gca | gcc | gcg | ggg | tac | tcc | ggt | 960 |
| Glu | Asp | Ala | Asn | Trp | Gly | Arg | Val | Ile | Ala | Ala | Ala | Gly | Tyr | Ser | Gly |
| 305 | | | | | 310 | | | | | 315 | | | | | 320 |

| gca | cag | ttc | gat | ccg | gac | aga | ctc | gac | ctt | ttc | ttc | gaa | agc | gca | gcc | 1008 |
| Ala | Gln | Phe | Asp | Pro | Asp | Arg | Leu | Asp | Leu | Phe | Phe | Glu | Ser | Ala | Ala |
| | | | | 325 | | | | | 330 | | | | | 335 | |

| ggt | aga | ata | aag | gtg | gca | gag | aac | ggc | cag | gga | gtg | gat | ttt | gac | gaa | 1056 |
| Gly | Arg | Ile | Lys | Val | Ala | Glu | Asn | Gly | Gln | Gly | Val | Asp | Phe | Asp | Glu |
| | | | 340 | | | | | 345 | | | | | 350 | | |

| gat | aca | gca | aag | aag | ata | ctg | agc | gaa | aag | agg | gtg | aaa | atc | atc | ctc | 1104 |
| Asp | Thr | Ala | Lys | Lys | Ile | Leu | Ser | Glu | Lys | Arg | Val | Lys | Ile | Ile | Leu |
| | | 355 | | | | | 360 | | | | | 365 | | | |

| gat | atg | aag | cag | gga | aaa | gaa | ctt | gca | aga | gcc | tgg | gga | tgt | gat | ctg | 1152 |
| Asp | Met | Lys | Gln | Gly | Lys | Glu | Leu | Ala | Arg | Ala | Trp | Gly | Cys | Asp | Leu |
| | 370 | | | | | 375 | | | | | 380 | | | | |

| act | gaa | aaa | tac | gtg | gaa | ata | aac | ggg | agg | tac | agg | aca | tga | | | 1194 |

-continued

Thr Glu Lys Tyr Val Glu Ile Asn Gly Arg Tyr Arg Thr
385             390             395

<210> SEQ ID NO 4
<211> LENGTH: 397
<212> TYPE: PRT
<213> ORGANISM: Thermotoga neapolitana

<400> SEQUENCE: 4

Val Phe Val Pro Arg Gly Phe Ser Tyr Ala Gly Val His Cys Arg Ile
1               5                   10                  15

Lys Arg Lys Arg Lys Asp Leu Gly Ile Ile Phe Ser Glu Val Pro Cys
            20                  25                  30

Thr Ala Ala Gly Val Phe Thr Thr Asn Val Val Lys Ala Ala Pro Val
        35                  40                  45

Ile Tyr Asp Met Glu Ile Leu Gly Lys Asn Pro Ser Gly Ile Arg Ala
    50                  55                  60

Ile Thr Val Asn Ser Gly Val Ala Asn Ala Cys Thr Gly Glu Gln Gly
65                  70                  75                  80

Met Ile Asn Ala Arg Arg Met Ala Glu Lys Thr Ala Lys Glu Leu Asn
                85                  90                  95

Ile Pro Val Glu Ser Val Leu Val Phe Ser Thr Gly Val Ile Gly Val
            100                 105                 110

Gln Leu Pro Met Glu Lys Val Glu Ser Gly Ile Glu Glu Ala Val Lys
        115                 120                 125

Asn Leu Ser Lys Asp Pro Val Pro Phe Ala Glu Ala Ile Met Thr Thr
130                 135                 140

Asp Thr Lys Ile Lys Ile His Ser Lys Lys Val Thr Ile Glu Gly Lys
145                 150                 155                 160

Glu Ile Thr Val Leu Gly Ile Ala Lys Gly Ser Gly Met Ile His Pro
                165                 170                 175

Asn Met Ala Thr Met Leu Ser Phe Ile Thr Thr Asp Ala Asn Val Ser
            180                 185                 190

Glu Asp Ala Leu Lys Lys Leu Leu Lys Ile Ser Val Asp Asp Ser Tyr
        195                 200                 205

Asn Met Ile Asp Val Asp Gly Asp Thr Ser Thr Asn Asp Met Val Ile
    210                 215                 220

Ile Leu Ala Asn Gly Leu Ala Gly Asn Ala Pro Ile Gln Glu Glu Thr
225                 230                 235                 240

Asp Gly Phe Trp Lys Leu Tyr Glu Ala Val His Glu Val Asn Gln Val
                245                 250                 255

Leu Ala Glu Lys Ile Val Glu Asp Gly Glu Gly Ala Thr Lys Val Ile
            260                 265                 270

Glu Val Glu Val Arg Asn Ala Pro Asp Arg Asn Ser Ala Arg Leu Ile
        275                 280                 285

Ala Arg Ala Ile Val Ser Ser Asn Leu Val Lys Pro Ala Ile Tyr Gly
    290                 295                 300

Glu Asp Ala Asn Trp Gly Arg Val Ile Ala Ala Gly Tyr Ser Gly
305                 310                 315                 320

Ala Gln Phe Asp Pro Asp Arg Leu Asp Leu Phe Phe Glu Ser Ala Ala
                325                 330                 335

Gly Arg Ile Lys Val Ala Glu Asn Gly Gln Gly Val Asp Phe Asp Glu
            340                 345                 350

Asp Thr Ala Lys Lys Ile Leu Ser Glu Lys Arg Val Lys Ile Ile Leu
        355                 360                 365

```
Asp Met Lys Gln Gly Lys Glu Leu Ala Arg Ala Trp Gly Cys Asp Leu
        370                 375                 380

Thr Glu Lys Tyr Val Glu Ile Asn Gly Arg Tyr Arg Thr
385                 390                 395

<210> SEQ ID NO 5
<211> LENGTH: 1209
<212> TYPE: DNA
<213> ORGANISM: Methanococcus jannaschii
<220> FEATURE:
<221> NAME/KEY: CDS
<222> LOCATION: (1)..(1209)
<223> OTHER INFORMATION:

<400> SEQUENCE: 5 atg aga gtt att gat ggt gga gtt aca gcc cct aag gga ttt aaa gcc      48
Met Arg Val Ile Asp Gly Gly Val Thr Ala Pro Lys Gly Phe Lys Ala
1               5                   10                  15 aat gga tac aaa gag ggt aag ttt gga gta gcg ata att atc tct gaa      96
Asn Gly Tyr Lys Glu Gly Lys Phe Gly Val Ala Ile Ile Ile Ser Glu
            20                  25                  30 aaa gat gca gta gga gct ggg aca ttc aca aca aat aaa gtt gta gct     144
Lys Asp Ala Val Gly Ala Gly Thr Phe Thr Thr Asn Lys Val Val Ala
        35                  40                  45 cat cct gta gtt tta tca agg gag ttg ata aaa aat aga gat aaa ttt     192
His Pro Val Val Leu Ser Arg Glu Leu Ile Lys Asn Arg Asp Lys Phe
    50                  55                  60 aga gca ata gtt gca aat agt gga aac gcc aac tgt ttt aca aaa gat     240
Arg Ala Ile Val Ala Asn Ser Gly Asn Ala Asn Cys Phe Thr Lys Asp
65                  70                  75                  80 gga atg gaa gat gct aaa gaa atg cag aga tta gta gca gag ctc ttt     288
Gly Met Glu Asp Ala Lys Glu Met Gln Arg Leu Val Ala Glu Leu Phe
                85                  90                  95 aat att aat gaa gat gag gtt tta gta gcc tca act gga gtt att gga     336
Asn Ile Asn Glu Asp Glu Val Leu Val Ala Ser Thr Gly Val Ile Gly
            100                 105                 110 aga aag atg gat atg aac att ata aaa gat aga ata aat aag gtt tat     384
Arg Lys Met Asp Met Asn Ile Ile Lys Asp Arg Ile Asn Lys Val Tyr
        115                 120                 125 aat tta ata aaa gaa gga aac agc tca ata aac gct gcc aaa gca ata     432
Asn Leu Ile Lys Glu Gly Asn Ser Ser Ile Asn Ala Ala Lys Ala Ile
    130                 135                 140 atg aca act gat aca aaa cca aag gaa ata gct gtg gag ttt gag gtt     480
Met Thr Thr Asp Thr Lys Pro Lys Glu Ile Ala Val Glu Phe Glu Val
145                 150                 155                 160 aat gga aaa act gtt aga gtt ggg gga ata gca aaa gga gct ggg atg     528
Asn Gly Lys Thr Val Arg Val Gly Gly Ile Ala Lys Gly Ala Gly Met
                165                 170                 175 ata gct cca aat atg tta cat gct act atg ctt tgc ttt ata aca aca     576
Ile Ala Pro Asn Met Leu His Ala Thr Met Leu Cys Phe Ile Thr Thr
            180                 185                 190 gac ata gag att gat aaa gaa agc tta aca aat atc ttg caa aag gtt     624
Asp Ile Glu Ile Asp Lys Glu Ser Leu Thr Asn Ile Leu Gln Lys Val
        195                 200                 205 gta gat aaa aca ttc aac aac ata tcc gtt gat gga gac act tca aca     672
Val Asp Lys Thr Phe Asn Asn Ile Ser Val Asp Gly Asp Thr Ser Thr
    210                 215                 220 aat gat acc gtt ttt gtt tta gct aat gga tta agt gga gtt aat tat     720
Asn Asp Thr Val Phe Val Leu Ala Asn Gly Leu Ser Gly Val Asn Tyr
225                 230                 235                 240
```

-continued

| | | |
|---|---|---|
| gaa gaa tgt gga gaa gag ttt gaa aat gcc tta ttg tat gtg tgc aga<br>Glu Glu Cys Gly Glu Glu Phe Glu Asn Ala Leu Leu Tyr Val Cys Arg<br>245 250 255 | | 768 |
| gag ctt gcc aag atg att gtt aag gat ggt gaa gga gct acc aaa ttt<br>Glu Leu Ala Lys Met Ile Val Lys Asp Gly Glu Gly Ala Thr Lys Phe<br>260 265 270 | | 816 |
| atg gag gtt gtt gtt aaa ggg gct aaa act gag gag gat gca gtt aaa<br>Met Glu Val Val Val Lys Gly Ala Lys Thr Glu Glu Asp Ala Val Lys<br>275 280 285 | | 864 |
| gca tca aag gct ata gtt aat tct ttg tta gtt aaa act gct gtg ttt<br>Ala Ser Lys Ala Ile Val Asn Ser Leu Leu Val Lys Thr Ala Val Phe<br>290 295 300 | | 912 |
| ggt gga gac cca aat tgg gga agg att gtt gct gct gtt gga tat agt<br>Gly Gly Asp Pro Asn Trp Gly Arg Ile Val Ala Ala Val Gly Tyr Ser<br>305 310 315 320 | | 960 |
| ggg gct gat ttc aac cca gaa gtt gtt gat gtt ata ttg agc aac tat<br>Gly Ala Asp Phe Asn Pro Glu Val Val Asp Val Ile Leu Ser Asn Tyr<br>325 330 335 | | 1008 |
| aaa gat gag gtt tat tta gtt aaa gat ggg att cca ttg gct gat gaa<br>Lys Asp Glu Val Tyr Leu Val Lys Asp Gly Ile Pro Leu Ala Asp Glu<br>340 345 350 | | 1056 |
| gga act gaa gag cta aaa aag gcc gag gag att atg aaa agt gat gaa<br>Gly Thr Glu Glu Leu Lys Lys Ala Glu Glu Ile Met Lys Ser Asp Glu<br>355 360 365 | | 1104 |
| ata aag ata gtt gtt gat ttg aag atg ggg gag ttt gag aac gtt tgt<br>Ile Lys Ile Val Val Asp Leu Lys Met Gly Glu Phe Glu Asn Val Cys<br>370 375 380 | | 1152 |
| tat gga tgt gat tta agc tat gag tat gtt aga ata aac gct gaa tat<br>Tyr Gly Cys Asp Leu Ser Tyr Glu Tyr Val Arg Ile Asn Ala Glu Tyr<br>385 390 395 400 | | 1200 |
| aca act taa<br>Thr Thr | | 1209 |

<210> SEQ ID NO 6
<211> LENGTH: 402
<212> TYPE: PRT
<213> ORGANISM: Methanococcus jannaschii

<400> SEQUENCE: 6

Met Arg Val Ile Asp Gly Gly Val Thr Ala Pro Lys Gly Phe Lys Ala
1               5                   10                  15

Asn Gly Tyr Lys Glu Gly Lys Phe Gly Val Ala Ile Ile Ser Glu
            20                  25                  30

Lys Asp Ala Val Gly Ala Gly Thr Phe Thr Thr Asn Lys Val Val Ala
        35                  40                  45

His Pro Val Val Leu Ser Arg Glu Leu Ile Lys Asn Arg Asp Lys Phe
    50                  55                  60

Arg Ala Ile Val Ala Asn Ser Gly Asn Ala Asn Cys Phe Thr Lys Asp
65                  70                  75                  80

Gly Met Glu Asp Ala Lys Glu Met Gln Arg Leu Val Ala Glu Leu Phe
                85                  90                  95

Asn Ile Asn Glu Asp Glu Val Leu Val Ala Ser Thr Gly Val Ile Gly
            100                 105                 110

Arg Lys Met Asp Met Asn Ile Ile Lys Asp Arg Ile Asn Lys Val Tyr
        115                 120                 125

Asn Leu Ile Lys Glu Gly Asn Ser Ser Ile Asn Ala Ala Lys Ala Ile
    130                 135                 140

Met Thr Thr Asp Thr Lys Pro Lys Glu Ile Ala Val Glu Phe Glu Val

```
                145                 150                 155                 160
Asn Gly Lys Thr Val Arg Val Gly Gly Ile Ala Lys Gly Ala Gly Met
                    165                 170                 175
Ile Ala Pro Asn Met Leu His Ala Thr Met Leu Cys Phe Ile Thr Thr
                180                 185                 190
Asp Ile Glu Ile Asp Lys Glu Ser Leu Thr Asn Ile Leu Gln Lys Val
            195                 200                 205
Val Asp Lys Thr Phe Asn Asn Ile Ser Val Asp Gly Asp Thr Ser Thr
        210                 215                 220
Asn Asp Thr Val Phe Val Leu Ala Asn Gly Leu Ser Gly Val Asn Tyr
225                 230                 235                 240
Glu Glu Cys Gly Glu Glu Phe Glu Asn Ala Leu Leu Tyr Val Cys Arg
                245                 250                 255
Glu Leu Ala Lys Met Ile Val Lys Asp Gly Glu Gly Ala Thr Lys Phe
                260                 265                 270
Met Glu Val Val Lys Gly Ala Lys Thr Glu Glu Asp Ala Val Lys
            275                 280                 285
Ala Ser Lys Ala Ile Val Asn Ser Leu Leu Val Lys Thr Ala Val Phe
        290                 295                 300
Gly Gly Asp Pro Asn Trp Gly Arg Ile Val Ala Ala Val Gly Tyr Ser
305                 310                 315                 320
Gly Ala Asp Phe Asn Pro Glu Val Val Asp Val Ile Leu Ser Asn Tyr
                325                 330                 335
Lys Asp Glu Val Tyr Leu Val Lys Asp Gly Ile Pro Leu Ala Asp Glu
            340                 345                 350
Gly Thr Glu Glu Leu Lys Lys Ala Glu Glu Ile Met Lys Ser Asp Glu
        355                 360                 365
Ile Lys Ile Val Val Asp Leu Lys Met Gly Glu Phe Glu Asn Val Cys
    370                 375                 380
Tyr Gly Cys Asp Leu Ser Tyr Glu Tyr Val Arg Ile Asn Ala Glu Tyr
385                 390                 395                 400
Thr Thr

<210> SEQ ID NO 7
<211> LENGTH: 37
<212> TYPE: DNA
<213> ORGANISM: Artificial Sequence
<220> FEATURE:
<223> OTHER INFORMATION: Synthetic DNA

<400> SEQUENCE: 7
gaaggagagt ataccatgac gatcacaaaa caaacgg                            37

<210> SEQ ID NO 8
<211> LENGTH: 38
<212> TYPE: DNA
<213> ORGANISM: Artificial Sequence
<220> FEATURE:
<223> OTHER INFORMATION: Synthetic DNA

<400> SEQUENCE: 8
gaaggagagt ataccatgtt cgttccgagg ggattcag                           38

<210> SEQ ID NO 9
<211> LENGTH: 37
<212> TYPE: DNA
<213> ORGANISM: Artificial Sequence
<220> FEATURE:
```

```
-continued

<223> OTHER INFORMATION: Synthetic DNA

<400> SEQUENCE: 9
gaaggagagt ataccatgag agttattgat ggtggag                              37

<210> SEQ ID NO 10
<211> LENGTH: 28
<212> TYPE: DNA
<213> ORGANISM: Artificial Sequence
<220> FEATURE:
<223> OTHER INFORMATION: Synthetic DNA

<400> SEQUENCE: 10
aaaggatcct tacgtccgat agctggcg                                       28

<210> SEQ ID NO 11
<211> LENGTH: 28
<212> TYPE: DNA
<213> ORGANISM: Artificial Sequence
<220> FEATURE:
<223> OTHER INFORMATION: Synthetic DNA

<400> SEQUENCE: 11
aaaggatcct catgtcctgt acctcccg                                       28

<210> SEQ ID NO 12
<211> LENGTH: 28
<212> TYPE: DNA
<213> ORGANISM: Artificial Sequence
<220> FEATURE:
<223> OTHER INFORMATION: Synthetic DNA

<400> SEQUENCE: 12
aaaggatcct taagttgtat attcagcg                                       28
```

MICROORGANISMS AND METHOD FOR L-ARGININE PRODUCTION BY FERMENTATION

TECHNICAL FIELD

The present invention relates to a new method for L-arginine production by fermentation.

L-arginine is an industrially useful amino acid as ingredient of liver function promoting agents, transfusion solutions, food additives and the like.

BACKGROUND OF THE ART

In microorganisms, biosynthesis of L-arginine proceeds in eight enzymatic steps starting from the precursor L-glutamate and follows two different pathways, the linear pathway or the cyclic acetyl pathway depending on the microorganism concerned (Cunin et al., 1986; Davis, 1986). In both biosynthetic pathways the first step is N-transacetylation of glutamate catalyzed by the enzymes displaying N-acetylglutamate synthase activity.

In the linear pathway, the acetylglutamate synthase activity is provided by the enzyme acetylCoA: L-glutamate N-acetyltransferase (EC 2.3.1.1.) encoded by the argA gene and in this pathway the intermediate N-acetyl L-ornithine is converted into L-ornithine at the fifth enzymatic step through deacetylation by $N^2$-acetyl-L-ornithine amidohydrolase (EC 3.5.1.16) encoded by the argE gene.

Thus, in microorganisms as Escherichia coli, L-arginine is synthesized from L-glutamate via N-acetylglutamate, N-acetylglutamylphosphate, N-acetylglutamate semialdehyde, N-acetylornithine, ornithine, citrulline and argininosuccinate. These intermediates are synthesized through consecutive reactions catalyzed by enzymes commonly known under the names N-acetylglutamate synthase, N-acetylglutamate kinase, N-acetylglutamylphosphate reductase, acetylornithine aminotransferase, N-acetylornithinase, ornithine carbamyltransferase, argininosuccinate synthase and argininosuccinase. These enzymes are encoded by argA, argB, argC, argD, argE, argF, argG and argH genes, respectively.

In the cyclic acetyl pathway, the acetyl-group of N-acetylornithine is transferred to L-glutamate by the enzyme ornithine acetyltransferase ($N^2$-acetyl-L-ornithine: L-glutamate N-acetyltransferase; EC 2.3.1.35) encoded by the argJ gene. Owning this enzyme, arginine biosynthetic pathway is recycled between the first and the fifth enzymatic steps and such a cyclic acetyl pathway is energetically advantageous over the linear pathway since N-acetyl ornithine can be used as the acetyl-group donor once the pathway is initiated from acetyl-CoA as a donor.

The cyclic acetyl pathway directs the L-arginine flow in procaryotic organisms as Corynebacterium glutamicum (Udaka and Kinoshita, 1958), cyanobacteria (Hoare and Hoare, 1966), Pseudomonas aeruginosa (Haas et al., 1972), Neisseria gonorrhoeae (Shinners and Catlin, 1978), methanogenic archaea (Meile and Leisinger, 1984), Thermotoga maritima (Van de Casteele et al., 1990), representatives of Bacillus (Sakanyan et al., 1992), Streptomyces coelicolor (Hindle et al., 1994), Thermus thermophilus (Baetens et al., 1998), an archaeon Methanococcus jannaschii (Marc et al., 2000) and in some eukaryotic organisms (De Deken, 1962). The nucleotide or amino acid sequences sharing similarity with the argJ gene or its product are also available for entirely or partially sequenced genomes and the similarity is indicative of the existence of the cyclic acetyl pathway in these organisms.

The argJ-encoded product, which exhibits the only ornithine acetyltransferase, is considered as a monofunctional enzyme and properties of such enzyme have been described (Haas et al., 1972; Sakanyan et al., 1996; Baetens et al., 1998; Marc et al., 2000). However, some microorganisms harbour the alternative version of the argJ gene encoding the enzyme which possesses, in addition to the ornithine acetyltransferase activity, the N-acetylglutamate synthase activity as well. Such genes and corresponding bifunctional enzymes have been described for Neisseria gonorrhoeae (Picard and Dillon, 1989; Martin and Mulks, 1992), B. stearothermophilus (Sakanyan et al., 1990 and, 1993), Saccharomyces cerevisiae (Crabeel et al., 1997), T. neapolitana (Marc et al., 2000).

The monofunctional ArgJ enzymes can be distinguished from bifunctional enzymes by two means: (i) by enzymatic assay using two acetyl-group donors, N-acetyl L-ornithine and acetyl-CoA; (ii) by complementation test using argE and argA mutants of Escherichia coli for the cloned argJ gene. The monofunctional ArgJ enzyme transfers the only acetyl group from N-acetyl L-ornithine to L-glutamate and complements the only argE mutant, whereas the bifunctional ArgJ enzyme transfers the acetyl-group both from N-acetyl L-ornithine and acetyl-CoA and complements both argE and argA mutant strains.

Both biosynthetic pathways are subjected to genetic and enzymatic regulation, respectively by a specific transcriptional repressor and by inhibition of enzymatic steps by L-arginine or intermediate products (Maas, 1994; Glansdorff, 1996). Moreover, the early metabolic steps preceding the L-glutamate precursor formation and late degradation steps following the L-arginine degradation are under the control of regulatory mechanisms. Consequently, synthesis of L-arginine and the production yield of this amino acid can be modulated by introduction of mutations at various targets in the genome of a given microorganism or by affecting the cultivation conditions of a given microorganism or by affecting the membrane permeability of a given microorganism.

Conventional L-arginine production by fermentation has been carried out using microbial strains producing L-arginine, especially representatives of coryneform bacteria; using coryneform bacteria resistant to certain antimetabolic agents including 2-thioazoalanine, α-amino-β-hydroxyvaleric acid, arginine hydroxamate, cysteine analogues, sulfonamide derivatives and the like; using coryneform bacteria exhibiting auxotrophy for some amino acids including for L-proline, L-histidine, L-threonine, L-isoleucine, L-methionine, or L-tryptophan, as well as using coryneform bacteria exhibiting both the mentioned above resistances and auxotrophies for amino acids. In this respect, reference may be made to the following patents: FR 2 084 059, 2 119 755, 2 490 674, 2 341 648, 2 225 519, EP 0 379903 B1, EP 0 378 223 B1, EP 0 336387 B1.

On the other hand, there have been disclosed methods for producing L-arginine by using a microorganism belonging to the genus Corynebacterium, Brevibacterium or Escherichia transformed by a recombinant DNA containing a well-defined gene of arginine biosynthesis that allows to enhance the gene-encoded enzyme activity for a given limiting step. The wild-type strain or the mutant for the transcriptional repressor or the mutant which carries a relevant resistance or auxotrophy have been used as recombinant host cell for fermentations.

Most of the recombinant microorganisms used for producing L-arginine belong to the genus *Corynebacterium* or *Brevibacterium*. In this respect, reference may be made to the following patents: FR 2 143 238; FR 2 484 448; EP 0 259858 B1; EP 0 261627 B1; EP 0 332233 A1; EP 0 999267 A1; EP 1016710 A2.

However, the *Escherichia coli* K12 strain, with the entirely sequenced genome (Blattner et al., 1997) and applicability of various genetic approaches and more advantageous vectors to manipulate in this strain or its derivatives, is an attractive host as well for the production of amino acids including L-arginine. The increased production of L-arginine by recombinant *Escherichia coli* strains can be achieved by using the cloned argA gene on plasmid vectors and followed by isolation of feed-back resistant mutations by the described method for *E. coli* (Eckhard and Leisinger, 1975; Rajagopal et al., 1998). In this respect, reference may be made to EP 1 016 710 A2.

Thus, L-arginine production by recombinant microorganisms has been improved by enhancing the number of copies of the gene coding for N-acetylglutamate synthase activity, namely by a wild type argA gene or its feedback resistant mutants.

However, the application of the mutant argA gene is limited in the context of a possibility of further increasing the productivity of L-arginine by recombinant strains.

It has now been found that it is possible to produce L-arginine with a microorganism having an L-arginine producing ability, said microorganism being a microorganism synthesizing L-arginine and bearing a recombinant DNA comprising a gene argJ coding an enzyme with an ornithine acetyltransferase activity.

SUMMARY OF THE INVENTION

The present invention provides a microorganism having L-arginine producing ability, which carries a recombinant DNA comprising an argJ gene encoding the ornithine acetyltransferase.

The present invention also provides the above mentioned microorganism, wherein the argJ gene codes for a monofunctional enzyme or preferably for a bifunctional enzyme. Preferably, the argJ gene codes for a mono— or bi-functional enzyme, devoid of inhibition by L-arginine.

More preferably, the argJ gene is derived from a thermophilic microorganism.

The present invention also provides a method for producing L-arginine comprising the steps of culturing the above mentioned microorganism in a medium to produce and accumulate L-arginine and collect L-arginine from the medium.

The term "L-arginine-producing ability" used in the present specification means the ability of the microorganism of the present invention to accumulate L-arginine in a culture medium when it is cultured in said medium.

DETAILED DESCRIPTION OF THE INVENTION

The microorganism of the present invention is a microorganism having L-arginine- producing ability, in which said ability is provided by the argJ gene encoding ornithine acetyltransferase introduced therein by recombinant DNA techniques.

Preferably, the argJ genes useful in the present invention are the genes encoding enzymes with ornithine acetyltransferase activity or enzymes with an ornithine acetyltransferase and N-acetylglutamate synthetase activities, said activities of the mono— or bi-functional enzymes being devoid of inhibition by L-arginine.

The argJ gene is advantageously derived from a thermophilic microorganism such as for example *Methanococcus jannasschii* or *Bacillus stearothermophilus* or *Thermotoga neapolitana*.

Sequences of said genes are disclosed in the following papers incorporated herein as reference:

argJ of *Methanococcus jannaschii*: Bult et al., 1996;

argJ of *Bacillus stearothermophilus* NCIB8224: Sakanyan et al., 1993;

argJ of *Thermotoga neapolitana*: Dimova et al., 2000

Examples of appropriate argJ genes are those derived from *Bacillus stearothermophilus* NCIB8224, ATCC12980, ATCC7953, ATCC10149, *Thermotoga neapolitana* DSM5068, ATCC49049, *Methanococcus jannaschii* DSM2661.

Preferred argJ genes are those derived from *Bacillus stearothermophilus* or *Thermotoga neapolitana*.

The microorganism producing L-arginine is any microorganism capable of synthesizing L-arginine through either the biosynthetic linear pathway or the cyclic pathway and which harbours the cloned argJ gene introduced therein by genetic engeenering.

Said microorganism may be selected for example from coryneform bacteria, such as those belonging to the genus Brevibacterium or the genus *Corynebacterium* or bacteria belonging to the genus *Escherichia*.

Preferably, said microorganism is a microorganism synthesizing arginine through the linear biosynthetic pathway and more particularly belongs to the genus *Escherichia*.

Examples of bacteria of the genus *Escherichia* appropriate for the present invention are listed as follows:

*Escherichia coli* K12 strain and its derivatives, notably *Escherichia coli* P4XB2(Hfr, metb, relA, argR) (Sakanyan et al., 1996). Said strain *Escherichia coli* P4XB2 was deposited at the "Collection Nationale de Culture de Microorganismes" (CNCM) of Pasteur Institute on Oct. 9, 2000, under number I 2571.

Preferably, the host strain is devoid of the transcriptional repression(argR⁻) involved in the negative control of L-arginine biosynthesis pathway in microorganims.

The argJ gene is amplified by PCR (polymerase chain reaction, see White T. J. et al. Trends Genet., 5, 185 (1989) utilising appropriate primers and thereafter ligated with a DNA vector according to the methods well-known to the man skilled in the art. Such methods are disclosed by Sambrook et al. in Molecular cloning Cold Spring Harbor Laboratory Press (1989).

The vector used for the cloning of argJ may be a plasmid autonomously replicable in the microorganisms with a low or moderated or high number of copies; a specific example thereof is the plasmid pACYC184 described in Sambrook et al., in Molecular cloning, Cold Spring Harbor Laboratory Press (1989). A phage vector may also be used. Integration of argJ gene onto the chromosomal DNA of the host bacterium can also be performed by homologous recombination without using any vector system. A shuttle vector autonomously replicable in different microorganisms synthesizing L-arginine may also be used for the introduction of argJ into the host cells other than *Escherichia*.

In order to prepare recombinant DNA molecules by ligating a gene carrying DNA fragment and a DNA vector, the vector is digested by restriction enzyme(s) corresponding to the termini of the amplified gene. Ligation is generally performed by using a ligase, such as T4DNA polynucleotide ligase.

The DNA vector is preferably an expression vector containing preferably a promoter, which may be followed by a ribosome binding site upstream of the gene to be expressed. This vector also contains an origin of replication and a selection marker.

The promoter may be weak or moderate or strong. The latter is subjected to a controlled action and provide, therefore a controlled gene expression. Appropriate promoters are for example tet or amp promoters and the like.

The selection marker is advantageously a gene responsible for resistance to antibiotics such as tetracyclin, ampicillin, chloramphenicol and the like.

The recombinant DNA comprising the appropriate means for the expression of the argJ gene in the microorganism concerned is introduced in that microorganism by conventional methods such as electroporation, $CaCl_2$-mediated transformation and the like.

According to a variant of embodiment of the invention, the microorganism of the invention may additionally harbour a recombinant DNA comprising the argA gene coding for N-acetylglutamate synthase and a DNA vector prepared according to the above methods. The argA gene can be taken from *Escherichia coli, Corynebacterium glutamicum, Pseudomonas aeruginosa* and the like.

Furthermore, the DNA vector may additionally contain a gene for utilization of a source of carbon other than glucose, such as a gene coding for sucrase, levanase, levane sucrase and the like, preferably a gene coding for levanase.

The method of the present invention for producing L-arginine comprises the steps of cultivating the microorganism of the present invention, in a culture medium, to produce and accumulate the amino acid in the medium, and recovering the amino acid from the medium.

In the method of the present invention, the cultivation of the microorganism belonging to the genus *Escherichia*, the collection and purification of amino acid from the liquid medium may be performed in a manner similar to those of the conventional methods for producing an amino acid by fermentation using a coryneform bacterium or *Escherichia coli* or *Bacillus subtilis*. A medium used for cultivation may be either a synthetic medium or a natural medium, so long as the medium includes a carbon and a nitrogen source and minerals, and, if necessary, nutrients which the bacterium used requires for growth in appropriate amounts. The carbon source may include various carbohydrates such as glucose and sucrose, and various organic acids. The carbon source is preferably sucrose. Depending on assimilatory ability of the used bacterium, alcohol including ethanol and glycerol may be used. As the nitrogen source, ammonia, various ammonium salts such as ammonium sulfate, other nitrogen compounds such as amines, a natural nitrogen source such as peptone, soybean hydrolyte and digested fermentative microbe are used. As minerals, mono-potassium phosphate, magnesium sulfate, sodium chloride, ferrous sulfate, manganese sulfate, calcium carbonate are used.

The cultivation is preferably carried out under aerobic conditions such as a shaking culture, and an aeration and stirring culture. The temperature of culture is usually 20 to 40° C., preferably 28 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 3-day cultivation leads to the accumulation of the given amino acid in the medium.

Recovering L-arginine can be performed by conventional methods, for example by removing solids such as cells from the medium by centrifugation or membrane filtration after cultivation, and then collecting and purifying L-arginine by ion exchange, concentration and crystalline fraction methods and the like.

The present invention will be now disclosed in more detail in the following examples given only for illustrative purposes.

EXAMPLE 1

Construction of Plasmids Carrying the argJ Gene

The following argJ genes cloned from the moderate thermophilic bacterium *Bacillus stearothermophilus* (Sakanyan el at., 1993) and the hyperthermophilic bacterium *Thermatoga neapolitana* (Dimova el al. 2000) have respectively the DNA sequences SEQ IN NO:1 and SEQ ID NO:3 which code for the proteins having the amino-acid sequences SEQ IN NO:2 and SEQ ID NO:4 respectively. The argJ sequence from the hyperthermophilic archaeon *Methanococcus jannaschii* (Bult et al., 1996) has the DNA sequence SEQ ID NO:5 which codes for the protein having the amino-acid SEQ ID NO:6. The primers corresponding to the 5' and 3' ends of the three argJ genes derived from these three microorganisms have been synthesized. The oligonucleotides corresponding to the beginning of the argJ gene containing a GGAG Shine/Dalgarno site have the following sequences:

BS 5'-GAAGGAGAGTATACCATGACGATCACAAAACAAACGG-3' SEQ ID NO:7)

TN 5'-GAAGGAGAGTATACCATGTTCGTTCCGAGGGGATTCAG-3' SEQ ID NO:8)

MJ 5'-GAAGGAGAGTATACCATGAGAGTTATTGATGGTGGAG-3' SEQ ID NO:9)

The oligonucleotides corresponding to the end of the argJ gene containing a GGATCC BamHI site have the following sequences:

BS 5'-AAAGGATCCTTACGTCCGATAGCTGGCG-3' SEQ ID NO:10)

TN 5'-AAAGGATCCTCATGTCCTGTACCTCCCG-3' SEQ ID NO:11)

MJ 5'-AAAGGATCCTTAAGTTGTATATTCAGCG-3' SEQ ID NO:12)

Amplification of the argJ gene from different DNA templates was carried out by PCR with DNA polymerase Pfu (Stratagene). The conditions used were as follows:

| Initial denaturation | 95° C., 5 min | |
|---|---|---|
| Denaturation | 94° C., 1 min | |
| Annealing | 47° C., 1 min | 30 cycles |
| Extension | 72° C., 2 min | |
| Final extension | 72° C., 7 min | 4° C. |

Figure 1:
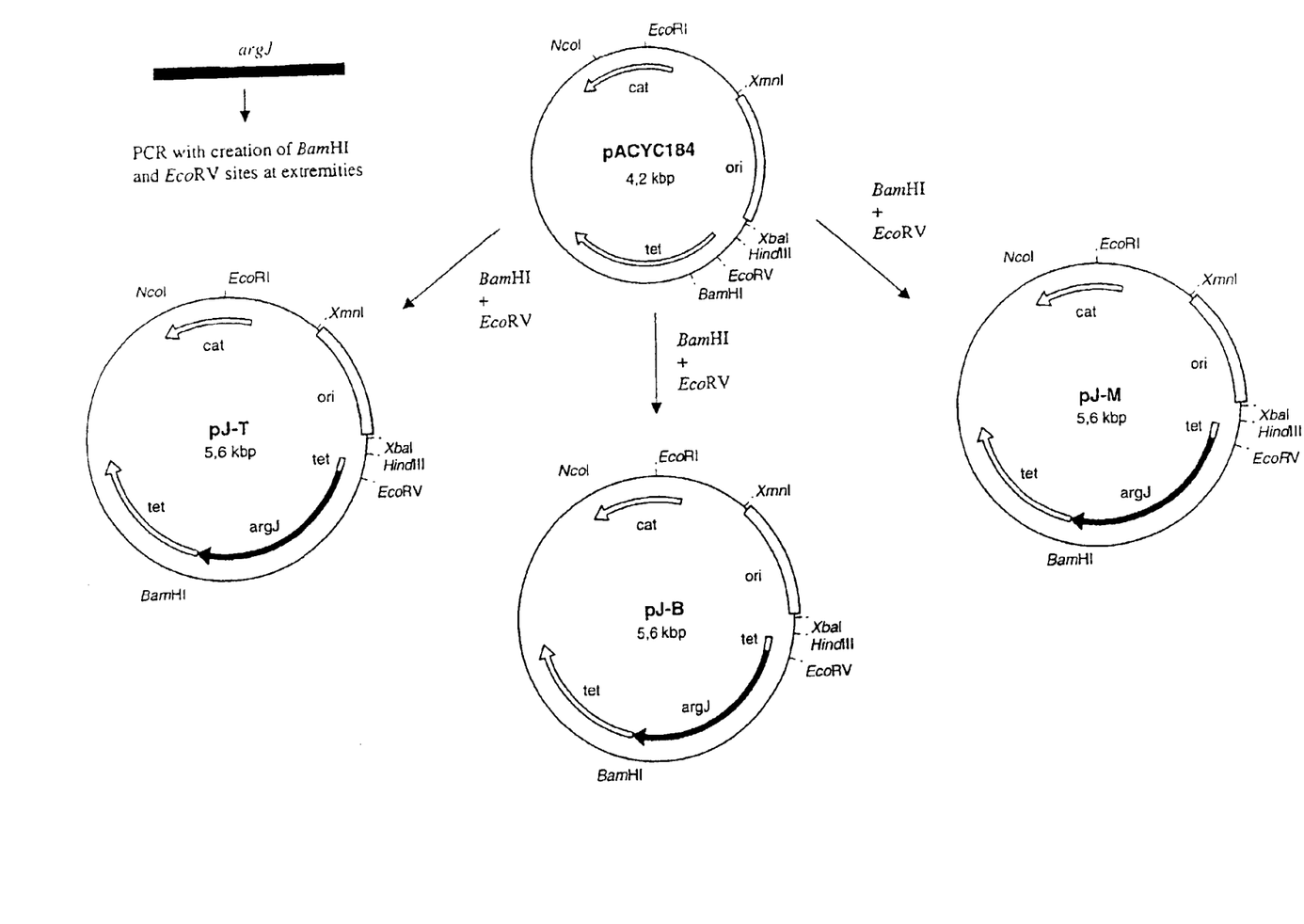
FIG. 1 is the restriction maps of plasmids pACYC184; pJ-B; pJ-T and pJ-M.

The PCR products were subsequently phosphorylated, digested with BamHI and then mixed with the plasmid vector pACYC184 preliminary digested with the enzyme EcoRV, dephosphorylated and then digested with the second enzyme BamHI. After ligation by T4 DNA ligase, the recombinant DNAs were transferred to the *Escherichia coli* K12 XS1D2R strain [F$^-$ Δ(ppc-argE) nalA rpoB λ$^-$ hsdR recA] by electroporation (2500 V, 21 μF, 400 Ω, 10 msec). The recombinant clones were selected on minimal medium M9 (Miller, 1992) without arginine solidified with agar (1.5%), supplemented with 0.2% of succinate and containing the antibiotic chloramphenicol (25 µg/ml). The Cm$^r$ ArgE$^+$ colonies were selected after three days of incubation at 37° C. and the recombinant plasmids carrying the argJ gene of the corresponding thermophilic microorganism were isolated from such clones. The plasmid DNAs obtained were sequenced to verify the cloned DNA sequences and the plasmids in which the argJ gene transcription is orientated under the control of the tet gene promoter were selected. Their restriction maps are shown in FIG. 1. The plasmids obtained, containing the argJ gene of *Bacillus stearothermophilus*, *Thermotoga neapolitana* or *Methanococcus jannaschii*, were called pJ-B, pJ-T and pJ-M respectively.

EXAMPLE 2

Genetic Analysis of the Recombinant Plasmids

By means of genetic and enzymatic analyses, it is possible to recognize the two types of the ArgJ enzyme. The monofunctional enzyme which possesses the only ornithine acetyltransferase activity is able to complement the argE mutant of *Escherichia coli* K12, whereas the bifunctional enzyme which exhibits both ornithine acetyltransferase activity and acetylglutamate synthase activity is able to complement the argE and argA mutants of *Escherichia coli* K12.

The three plasmids obtained were transferred by electroporation to the *Escherichia coli* K12 XA4 strain, which bears the single argA mutation and to the double mutant *Escherichia coli* K12 XA4::argE strain, which bears the argA and argE mutations, using the conditions described in Example 1. The recombinant colonies were selected on LB rich medium solidified with agar (1.2%) and containing the antibiotic chloramphenicol (25 µg/ml). 50 colonies from each dish were resuspended in NaCl solution (0.9%) and then replicated on dishes with a minimal medium M9 solidified with agar (1.2%) and with or without L-arginine (150 µg/ml) but always containing chloramphenicol (25 µg/ml). After two days of incubation at 37° C., all 50 clones of the *Escherichia coli* K12 strains XA4(pJ-B), XA4::argE (pJ-B), XA4(pJ-T) and XA4::argE(pJ-T) developed on the selective media described. By contrast, no colonies of the *Escherichia coli* K12 strains XA4(pJ-M) and XA4::argE(pJ-M) grew on arginine-free medium, whereas they were clearly visible after two days on medium supplemented with L-arginine These results indicate that the argJ gene of *Bacillus stearothermophilus* and *Thermotoga neapolitana* codes for a bifunctional enzyme, whereas the argJ gene of *Methanococcus jannaschii* codes for a monofunctional enzyme.

EXAMPLE 3

Enzymatic Analysis

The *Escherichia coli* K12 strains XS1D2(pJ-B), XS1D2 (pJ-T) and XS1D2(pJ-M) were cultivated in a minimal medium M9 devoid of arginine, but supplemented with succinate (0.2%) and containing chloramphenicol (25 µg/ml), at 37° C. for 24 hours. The cells were then pelleted, washed twice in Tris-HCl buffer (0.1 M, pH 8) and then lyzed by sonication (15 min per pulse of 10 s at 19 kHz). The enzymatic activities were measured in the following buffer: 0.1 M MES, 0.1 M PIPES, 0.1 M Tris, 0.1 M glycine and 0.1 M K$_2$HPO$_4$, using as an acetyl-group donor, acetyl CoA or N-acetyl ornithine at 37° C. or at 70° C., and the reaction product, i.e. N-acetylglutamate, was quantified by HPLC. The samples were analyzed on a Luna C18 column (Phenomenex) on an HPLC system (Kontron) using a mixture of 0.1 M phosphoric acid and methanol (90:10 v:v) with a flow rate of 1 ml/min as the mobile phase. The reaction product was detected at 215 nm. The results given in Table 1 show that the three enzymes possess the ornithine acetyltransferase activity at 37° C. and 70° C.

TABLE 1

Ornithine acetyltransferase and acetylglutamate synthase activities (µmoles · min$^{-1}$ · mg$^{-1}$ protein) measured at 37° C. and 70° C. for recombinant thermostable ArgJ enzymes

| Strain/plasmid | 37° C. | | | | 70° C. | |
|---|---|---|---|---|---|---|
| | Ornithine acetyltransferase activity | Ornithine acetyltransferase activity in the presence of 10 mM of L-arginine | Acetylglutamate synthase activity | Acetylglutamate synthase activity in the presence of 10 mM of L-arginine | Ornithine acetyltransferase activity | Acetylglutamate synthase activity |
| XS1D2 (pJ-B) | 4 | 4 | 0.5 | 0.5 | 25 | 2 |
| XS1D2 (pJ-T) | 5 | 5 | 0.4 | 0.4 | 190 | 7 |
| XS1D2 (pJ-M) | 4.5 | 4.5 | 0 | 0 | 165.5 | 0 |

The acetylglutamate synthase activity was detected only for the enzymes of *Bacillus stearothermophilus* and *Thermotoga neapolitana* at both temperatures. These results confirm that the ArgJ enzymes from *Bacillus stearothermophilus* and *Thermotoga neapolitana* are indeed bifunctional enzymes, whereas that from *Methanococcus jannaschii* is a monofunctional enzyme. No decreasing of enzymatic activities was detected by addition of 10 mM L-arginine.

EXAMPLE 4

L-arginine Production by Recombinant *Escherichia coli* K12 P4XB2 Strains

Plasmids pJ-B, pJ-T and pJ-M were transferred to the *Escherichia coli* K12 P4XB2 strain by electroporation under the conditions described above in Example 1. The corresponding clones were selected on LB rich medium solidified with agar (1.2%) and containing chloramphenicol (25 μg/ml). Three independent colonies of each recombinant strain were chosen for evaluating the amount of L-arginine produced during the fermentations. For this purpose the colonies, taken from the dishes were resuspended in a LB medium containing chloramphenicol and cultivated at 30° C. until the optical density reached 0.8 at 600 nm. 1 ml of this preculture was added to 14 ml of fermentation medium having the following composition: 2.8% of $(NH_4)_2SO_4$, 0.2% of $K_2HPO_4$, 0.5% of yeast extract, 0.05% of $MgSO_4$, 0.001% of $FeSO_4$, 0.001% of $MnSO_4$, 10 μg/ml of thiamine, 100 μg/ml of methionine, 5% of glucose, 2.5% of $CaCO_3$, 25 μg/ml of chloramphenicol; pH 7.2. The fermentation was performed in 750 ml conical flasks on a circular shaker at a speed 320 rpm at 30° C. for 40 h. After fermentation, the samples were recovered and the amount of L-arginine was evaluated against a L-arginine calibration-scale, either by paper chromatography or by thin layer chromatography and developing with 0.5% of ninhydrin dissolved in acetone or by spectrophotometry or by an amino acid analyzer. The results of these fermentations are presented in Table 2.

TABLE 2

Production of L-arginine by the
Escherichia coli K12 P4XB2 strain and its recombinant
derivatives harbouring the cloned argJ gene

| Strain/plasmid | L-arginine (g/l) |
| --- | --- |
| P4XB2 | <0.2 |
| P4XB2 (pJ-M) | 0.5 |
| P4XB2 (pJ-B) | 9.0 |
| P4XB2 (pJ-T) | 9.0 |

These results revealed that all the argJ-carrying plasmids possess the capacity to increase the yield of L-arginine in Escherichia coli K12 host cells. Obviously, this level of production of L-arginine in Escherichia coli is much greater in those strains which contain plasmids pJ-B or pJ-T as compared with the Escherichia coli K12 strains which contain the pJ-M plasmid. This demonstrates that expression of the gene coding for the bifunctional ArgJ enzyme ensures a greater production yield of L-arginine, compared with the gene coding for a monofunctional ArgJ enzyme.

EXAMPLE 5

Synthesis of L-arginine in the Escherichia coli K 12 Strain Carrying Two Plasmids The plasmid pARG2S makes it possible to produce L-arginine in Escherichia coli K12. This plasmid carries the argA gene from Escherichia coli K12 and the levanase gene (sacC) from Bacillus subtilis Marburg 168 on the pBR327-kan vector. The wild-type argA gene from Escherichia coli K12 was cloned by complementation of the argA mutant of Escherichia coli K12 (Nersisyan et al., 1986). The sacC gene from Bacillus subtilis Marburg 168 was selected in the pQB79,1 cosmid bank (Fouet et al., 1982) by using a minimal medium M9 containing sucrose as a sole carbon source. The sacC gene identified within a 6.7 kb EcoRI-HindIII DNA fragment was inserted in the plasmid pBR327-kan digested by EcoRI and HindIII. Then, a 1.5 kb BamHI-SalI DNA fragment carrying argA was inserted in the obtained plasmid digested by BamHI and SalI by selection of recombinant clones bearing the pARGS2 plasmid. The pARGS2 plasmid ensures the growth of Escherichia coli K12 argA mutant cells on a selective medium M9 with sucrose as a sole carbon source, without or with L-arginine.

Plasmids pJ-B, pJ-T and pJ-M were transferred to the Escherichia coli K12 P4XB2(pARGS2) strain and the recombinant clones were selected on LB medium containing the two antibiotics, chloramphenicol (25 μg/ml) and kanamycin (40 μg/ml). Three colonies of each transformed strain and of the original strain were tested for the production of L-arginine under the conditions used in Example 4, except that the medium contained the only kanamycin (40 μg/ml) for Escherichia coli K12 P4XB2(pARGS2) or kanamycin in addition to the composition described for transformed clones.

The results of the fermentations are given in Table 3.

TABLE 3

Production of L-arginine by the
Escherichia coli K12 P4XB2 strain carrying the plasmid
pARGS2 alone or in combination with pJ-M, pJ-B or pJ-T.

| Strain/plasmid | L-arginine (g/l) |
| --- | --- |
| P4XB2 | <0.2 |
| P4XB2 (pARGS2) | 6.5 |
| P4XB2 (pARGS2/pJ-M) | 7.0 |
| P4XB2 (pARGS2/pJ-B) | 13 |
| P4XB2 (pARGS2/pJ-T) | 13 |

These results demonstrate that the concomitant presence of any of the three plasmids carrying the argJ gene along with the pARGS2 plasmid in the same Escherichia coli host strain provides higher production of L-arginine. However, the L-arginine yield is greater in the Escherichia coli K12 P4XB2 strain harbouring pARGS2 and pJ-B or pJ-T plasmids than in the Escherichia coli K12 P4XB2 strain harbouring pARGS2 and pJ-M plasmids. These results reveal that the co-existence of the argA gene (the pARGS2 plasmid)with the argJ gene coding for the bifunctional enzyme ornithine acetyltransferase (the pJ-B or pJ-T plasmids) in the same strain, assures a greater yield of L-arginine than with the argJ gene coding for a monofunctional enzyme (the pJ-M plasmid).

EXAMPLE 6

Production of L-arginine in a Fermentation Medium Containing Sucrose

Plasmid pARGS2 enables the Escherichia coli K12 cells to consume sucrose as a carbon source. The wild-type Escherichia coli K12 strain and its derivatives are naturally unable of developing in a minimal medium in which glucose is replaced with sucrose.

The strains described in Example 5 were used to perform fermentations for the production of L-arginine under the conditions described above, except that the glucose is replaced with sucrose (6%) and the cultivation was prolonged for 44 h. The results are given in Table 4.

TABLE 4

Production of L-arginine by recombinant
Escherichia coli K12 P4XB2 strains on sucrose-
containing fermentation medium

| Strain/plasmid | L-arginine (g/l) |
| --- | --- |
| P4XB2 | <0.2 |
| P4XB2 (pARGS2) | 8.5 |
| P4XB2 (pARGS2/pJ-M) | 8.5 |
| P4XB2 (pARGS2/pJ-B) | 14.0 |
| P4XB2 (pARGS2/pJ-T) | 14.0 |

These results again reveal that the bifunctional ArgJ enzyme as compared with the monofunctional enzyme provides higher yields of L-arginine in *Escherichia coli* K12 strains carrying the second plasmid pARGS2 with the argA and the sucrose-consumpting gene sacC during fermentation in a medium in which glucose is replaced by sucrose.

REFERENCES

Baetens, M., Legrain, C., Boyen, A., & Glansdorff, N. (1998) Genes and enzymes of the acetyl cycle of arginine biosynthesis in the extreme thermophilic bacterium *Thermus thermophilus*. Microbiology 144, 479–492.

Blattner, F. R. et al. (1997) The complete genome sequence of *Escherichia coli* K-12. Science, 277, 1453–1462.

Bult, C. J. et al. (1996) Complete genome sequence of the methanogenic archaeon, *Methanococcus jannaschii*. Science 273, 1058–1073.

Crabeel, M., Abadjieva A., Hilven P., Desimpelaere J., & Soetens O. (1997) Characterization of the *Saccharomyces cerevisiae* ARG7 gene encoding ornithine acetyltransferase, an enzyme also endowed with acetylglutamate synthase activity. Eur. J. Biochem. 250, 232–241.

Cunin, R., Glansdorff, N., Pierard, A., & Stalon, V. (1986) Biosynthesis and metabolism of arginine in bacteria. Microbiol. Rev. 50, 314–352.

Davis, R. H. (1986) Compartmental and regulatory mechanisms in the arginine pathways of *Neurospora crassa* and *Saccharomyces cerevisiae*. Microbiol. Rev. 50, 280–313.

De Deken, R. H. (1962) Biosynthese de l'arginine chez la levure. 1. Le sort de la $N^\alpha$-acétylornithine. Biochim. Biphys. Acta. 78, 606–616.

Dimova, D., Weigel, P., Takahashi, M., Marc, F., Van Duyne, G. D., & Sakanyan, V. (2000) Thermostability, oligomerization and DNA binding properties of the ArgR regulatory protein from hyperthermophilic bacterium *Thermotoga neapolitana*. Mol. Gen. Genet. 263, 119–130.

Eckhardt, T. & Leisinger, T. (1975) Isolation and characterization of mutants with a feedback resistant N-acetylglutamate synthesis in *Escherichia coli* K12. Mol. Gen. Genet. 138, 225–232.

Fouet, A., Klier, A. & Rapoport, G. (1982) Cloning and expression in *Escherichia coli* of the sucrase gene from *Bacillus subtilis*. Mol. Gen. Genet. 186, 399–404.

Glansdorff, N. (1996) Biosynthesis of arginine and polyamines. In *Escherichia coli* and Salmonella: cellular and molecular biology (Neidhardt, F. C., Ed. in chief), pp. 408–433, American Society for Microbiology Press, Washington, DC.

Haas, D., Kurer, V. & Leisinger, T. (1972) N-acetylglutamate synthase of *Pseudomonas aeruginosa*. An assay in vitro and feedback inhibition by arginine. Eur. J. Biochem. 31, 290–295.

Hindle, Z., Callis, R., Dowden, S., Rudd, B. A., & Baumberg, S. (1994) Cloning and expression in *Escherichia coli* of a *Streptomyces coelicolor* A3(2) argCJB gene cluster. Microbiology 140, 311–320.

Hoare, D. S. & Hoare, S. L. (1966) Feedback regulation of arginine biosynthesis in blue-green algae and photosynthetic bacteria. J. Bacteriol. 92, 375–379.

Maas, W. (1994) The arginine repressor of *Escherichia coli*. Microbiol. Rev. 58, 631–640.

Marc, F., Weigel, P., Legrain, C., Almeras, Y., Santrot, M., Glansdorff, N. & Sakanyan, V. (2000) Characterization and kinetic mechanism of mono- and bifunctional ornithine acetyltransferaes from thermophilic microorganisms. Eur. J. Biochem. 267, 5217–5226.

Martin, P. R. & Mulks, M. H. (1992) Sequence analysis and complementation studies of the argJ gene encoding ornithine acetyltransferase from *Neisseria gonorrhoeae*. J Bacteriol 174, 2694–2701.

Meile, L., & Leisinger, T. (1984) Enzymes of arginine biosynthesis in methanogenic bacteria. Experientia 40, 899–900.

Miller, J. H. (1992) A short course in bacterial genetics. Cold Spring Harbor Labor. Press, Cold Spring Harbor Labor.

Nersisyan, A. A., Mett, I. L., Badalyan, Z. R., Kochikyan, A. V., Mett, A. L., Kocharyan, A. M., Kocharyan, S. M. & Sakanyan, V. A. (1986) Genetika (USSR) 22, 1061–1066.

Picard, F. J. & Dillon, J. R. (1989) Cloning and organization of seven arginine biosynthesis genes from *Neisseria gonorrhoeae*. J Bacteriol 171, 1644–1651.

Rajagopal, B. S., DePonte III, J., Tuchman, M. & Malamy, M. H. (1998) Use of inducible feed-resistant N-acetylglutamate synthetase (argA) genes for enhanced arginine biosynthesis by genetically engineered *Escherichia coli* K-12 strains. Appl. Environ. Microbiol. 64, 1805–1811.

Sakanyan, V. A., Hovsepyan, A. S., Mett, I. L., Kochikyan, A. V., & Petrosyan, P. K. (1990) Molecular cloning and structural-functional analysis of arginine biosynthesis genes of the thermophilic bacterium *Bacillus stearothermophilus*. Genetika (USSR) 26, 1915–1925.

Sakanyan, V., Kochikyan, A., Mett, I., Legrain, C., Charlier, D., Pierard A., & Glansdorff, N. (1992) A re-examination of the pathway for ornithine biosynthesis in a thermophilic and two mesophilic Bacillus species. J. Gen. Microbiol. 138, 125–130.

Sakanyan, V., Charlier, D., Legrain, C., Kochikyan, A., Mett, I., Pierard, A., & Glansdorff, N. (1993) Primary structure, partial purification and regulation of key enzymes of the acetyl cycle of aginine biosynthesis in *Bacillus stearothermophilus:* dual function of ornithine acetyltransferase. J. Gen. Microbiol. 139, 393–402.

Sakanyan, V., Petrosyan, P., Lecocq, M., Boyen, A., Legrain, C., Demarez, M., Hallet, J. N., & Glansdorff, N. (1996) Genes and enzymes of the acetyl cycle of arginine biosynthesis in *Corynebacterium glutamicum:* enzyme evolution in the early steps of the arginine pathway. Microbiology 142, 99–108.

Shinners, E. N., & Catlin, B. W. (1978) Arginine biosynthesis in *Neisseria gonorrhoeae:* enzymes catalyzing the formation of ornithine and citrulline. J. Bacteriol. 136, 131–135.

Udaka, S., & Kinoshita S. (1958) Studies on L-ornithine fermentation. I. The biosynthetic pathway of L-ornithine in *Micrococcus glutamicus*. J. Gen. Appl. Microbiol. 4, 272–282.

Van de Casteele, M., Demarez, M., Legrain, C., Glansdorff, N., & Pierard, A. (1990) Pathways of arginine biosynthesis in extreme thermophilic archaeo-and eubacteria. J. Gen. Microbiol. 136, 1177–1183.

What is claimed is:

1. A transformed bacterium having an L-arginine producing ability, said bacterium being a bacterium synthesizing L-arginine through the biosynthetic linear or cyclic pathway, and bearing a recombinant DNA comprising a gene argJ coding for an enzyme having an ornithine acetyltransferase activity as set forth in SEQ ID NO:2 and wherein said bacterium is free of arginine repression.

2. A transformed bacterium having an L-arginine producing ability, said bacterium being a bacterium synthesizing L-arginine through the biosynthetic linear pathway, and bearing a recombinant DNA comprising a gene argJ coding for an enzyme having an ornithine acetyltransferase activity as set forth in SEQ ID NO:2 and wherein said bacterium is free of arginine repression.

3. The bacterium according to claim 1, wherein the argJ gene codes for a bifunctional enzyme having both ornithine acetyltransferase activity and acetylglutamate synthetase activity.

4. The bacterium according to claim 1, wherein the enzyme is devoid of inhibition by L-arginine.

5. A transformed bacterium having a L-arginine producing ability, said bacterium synthesizing L-arginine through biosynthetic linear or cyclic pathway and bearing a recombinant DNA comprising a gene argJ encoding for a bifunctional enzyme with an ornithine acetyltransferase activity and acetylglutamate synthetase activity as set forth in SEQ ID NO:2 and wherein said bacterium is free of arginine repression.

6. The bacterium according to claim 1, wherein belongs to the genus Escherichia coli.

7. The bacterium according to claim 1, wherein the argJ gene is derived from a thermophilic bacterium.

8. The bacterium according to claim 1, wherein the argJ gene is derived from the thermophilic bacterium belonging to the species *Bacillus stearothermophilus* and *Thermotoga neapolitana*.

9. The bacterium according to claim 1, which harbours a further recombinant DNA comprising gene a argA coding for the N-acetylglutamate synthetase.

10. A method for producing L-arginine comprising the steps of cultivating the bacterium as defined in claim 1, in a culture medium to produce and accumulate L-arginine in the medium and recovering L-arginine from the medium.

11. The bacterium according to claim 2, wherein the argJ gene codes for a bifunctional enzyme having both ornithine acetyltransferase activity and acetylglutamate synthetase activity.

12. The bacterium according to claim 2, wherein the enzyme is devoid of inhibition by L-arginine.

13. The bacterium according to claim 2, wherein the argJ gene is derived from the thermophilic bacterium belonging to the species *Bacillus stearothermophilus* and *Thermotoga neapolitana*.

14. The bacterium according to claim 2, which harbours a further recombinant DNA comprising gene a argA coding for the N-acetylglutamate synthetase.

15. A method for producing L-arginine comprising the steps of cultivating the bacterium as defined in claim 2, in a culture medium to produce and accumulate L-arginine in the medium and recovering L-arginine from the medium.

16. The bacterium according to claim 5, wherein the argJ gene is derived from the thermophilic bacterium belonging to the species *Bacillus stearothermophilus* and *Thermotoga neapolitana*.

17. The bacterium according to claim 5, which harbours a further recombinant DNA comprising gene a argA coding for the N-acetylglutamate synthetase.

18. A method for producing L-arginine comprising the steps of cultivating the bacterium as defined in claim 5, in a culture medium to produce and accumulate L-arginine in the medium and recovering L-arginine from the medium.

* * * * *